US010646573B2

(12) United States Patent
Warashina et al.

(10) Patent No.: US 10,646,573 B2
(45) Date of Patent: *May 12, 2020

(54) COMPOSITION FOR HOT MELT EXTRUSION AND METHOD FOR PRODUCING HOT MELT EXTRUDATE BY USING SAME

(71) Applicant: SHIN-ETSU CHEMICAL CO., LTD., Tokyo (JP)

(72) Inventors: Shogo Warashina, Niigata (JP); Fumie Kusaki, Niigata (JP); Sakae Obara, Tokyo (JP); Kazuki Kikuchi, Niigata (JP); Naosuke Maruyama, Niigata (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/892,421

(22) PCT Filed: Jun. 3, 2014

(86) PCT No.: PCT/JP2014/064711
§ 371 (c)(1),
(2) Date: Nov. 19, 2015

(87) PCT Pub. No.: WO2014/196519
PCT Pub. Date: Dec. 11, 2014

(65) Prior Publication Data
US 2016/0095928 A1  Apr. 7, 2016

(30) Foreign Application Priority Data

Jun. 3, 2013 (JP) ................................ 2013-116836
Nov. 28, 2013 (JP) ................................ 2013-246178

(51) Int. Cl.
| | | |
|---|---|---|
| A61K 47/38 | (2006.01) | |
| A61K 9/14 | (2006.01) | |
| A61K 31/4422 | (2006.01) | |
| C08J 3/20 | (2006.01) | |
| C08B 11/193 | (2006.01) | |
| C08B 11/20 | (2006.01) | |
| C08B 13/00 | (2006.01) | |
| C08L 1/32 | (2006.01) | |
| A61K 31/496 | (2006.01) | |

(52) U.S. Cl.
CPC .............. *A61K 47/38* (2013.01); *A61K 9/146* (2013.01); *A61K 31/4422* (2013.01); *A61K 31/496* (2013.01); *C08B 11/193* (2013.01); *C08B 11/20* (2013.01); *C08B 13/00* (2013.01); *C08J 3/201* (2013.01); *C08L 1/32* (2013.01); *C08J 2301/32* (2013.01)

(58) Field of Classification Search
None
See application file for complete search history.

(56) References Cited

U.S. PATENT DOCUMENTS

| | | | |
|---|---|---|---|
| 3,852,421 A | 12/1974 | Koyanagi et al. | |
| 4,226,981 A | 10/1980 | Onda et al. | |
| 4,266,981 A | 5/1981 | Tsao et al. | |
| 8,207,232 B2 | 6/2012 | Babcock et al. | |
| 10,016,508 B2 * | 7/2018 | Warashina ......... | A61K 31/4422 |
| 2003/0186952 A1 | 10/2003 | Crew et al. | |
| 2008/0262107 A1 | 10/2008 | Babcock et al. | |
| 2011/0034478 A1 | 2/2011 | Fang et al. | |
| 2011/0123627 A1 | 5/2011 | Fang et al. | |
| 2012/0252819 A1 | 10/2012 | Padval et al. | |
| 2013/0102691 A1 | 4/2013 | Miller et al. | |

FOREIGN PATENT DOCUMENTS

| | | |
|---|---|---|
| CN | 102065842 A | 5/2011 |
| EP | 2 810 660 A1 | 12/2014 |
| EP | 3 006 049 A1 | 4/2016 |
| JP | 54-61282 A | 5/1979 |
| JP | 2004-262999 A | 9/2004 |
| JP | 2005-523895 A | 8/2005 |
| JP | 2008-501009 A | 1/2008 |
| JP | 2011-516612 A | 5/2011 |
| JP | 2013-116836 | 6/2013 |
| WO | WO 2003/063832 A1 | 8/2003 |
| WO | WO 03/077827 A1 | 9/2003 |
| WO | WO 2005/115330 A2 | 12/2005 |
| WO | WO 2007/029660 A1 | 3/2007 |
| WO | WO 2008/051794 A2 | 5/2008 |
| WO | WO 2009/129300 A2 | 10/2009 |
| WO | WO 2011/159626 A1 | 12/2011 |
| WO | WO-2012/122279 | 9/2012 |
| WO | WO 2014/031422 A1 | 2/2014 |

OTHER PUBLICATIONS

Chen, R., et al. "Hypromellose Acetate Succinate" in Handbook of Pharmaceutical Excipients. Pharmaceutical Press and American Pharmacists Association 2009 (6th Edition) 330-332.*
Tanno, Fumié, et al. "Evaluation of hypromellose acetate succinate (HPMCAS) as a carrier in solid dispersions." Drug development and industrial pharmacy 30.1 (2004): 9-17.*
Crowley, Michael M., et al. "Pharmaceutical applications of hot-melt extrusion: part I." Drug development and industrial pharmacy 33.9 (2007): 909-926.*

(Continued)

*Primary Examiner* — Bethany P Barham
*Assistant Examiner* — Peter Anthopolos
(74) *Attorney, Agent, or Firm* — Rimon, P.C.

(57) ABSTRACT

Provided is a composition for hot melt extrusion including a drug and hypromellose acetate succinate (HPMCAS) having a hydroxypropoxy molar substitution of 0.40 or more and a mole ratio of an acetyl group to a succinyl group of less than 1.6. Further, provided is a method for producing a hot melt extrudate including the step of hot melt-extruding a composition for hot melt extrusion including a drug and hypromellose acetate succinate having a molar hydroxypropoxy substitution of 0.40 or more and a mole ratio of an acetyl group to a succinyl group of less than 1.6, at a hot melt temperature of not lower than a melting temperature of the hypromellose acetate succinate or of not lower than a temperature at which both the hypromellose acetate succinate and the drug are melted.

10 Claims, No Drawings

(56) References Cited

OTHER PUBLICATIONS

Fukasawa, Miyuki, and Sakae Obara. "Molecular weight determination of hypromellose acetate succinate (HPMCAS) using size exclusion chromatography with a multi-angle laser light scattering detector." Chemical and pharmaceutical bulletin 52.11 (2004): 1391-1393.*

Nakamichi, K., et al. "The preparation of enteric solid dispersions with hydroxypropylmethylcellulose acetate succinate using a twin-screw extruder." Journal of Drug Delivery Science and Technology 14.3 (2004): 193-198.*

Liang-liang, Z. et al., *Determination of Acyl Content in Hydroxypropyl Methylcellulose Acetate Succinate by High Performance Liquid Chromatography* (Apr. 30, 2012), 71-75.

Office Action for Chinese Application No. 201410242677.6 dated Mar. 9, 2016.

Office Action from European Patent Application No. 14170863.6 dated Jun. 1, 2016.

"Hypromellose Acetate Succinate" Supp I, JP SVI, Official Monographs, Japanese Pharmacopoeia 16th Edition (Sep. 27, 2012), pp. 2426-2428.

Extended European Search Report from corresponding European Patent Application No. 14170863.6 dated Sep. 17, 2014.

Floyd F L Ho, et al.; "Determination of Molar Substitution and Degree of Substitution of Hydroxypropyl Cellulose by Nuclear Magnetic Resonance Spectrometry"; Analytical Chemistry; American Chemical Society; vol. 44, No. 1; Jan. 1, 1972; pp. 178-181; XP55139137.

Obara et al.; "Application Studies of L-HPC and HPMCAS for Pharmaceutical Dosage Forms" (google date of Apr. 2012).

International Search Report and Written Opinion from International Application No. PCT/JP2014/064711 dated Sep. 9, 2014.

Extended European Search Report from corresponding European Patent Application No. 14806945.3 dated Jan. 25, 2017, 6 pages.

Notice of Opposition for European Applcation No. 14170863.6 dated May 4, 2018, 6 pages.

Opponent's Letter in Opposition for European Application No. 14170863.6 dated Apr. 17, 2018, 12 pages.

Specification for Japanese Application No. 2013-2461778 filed Nov. 28, 2013, 26 pages.

Notice of Opposition to a European Patent No. EP 3 006 049 B1 dated Nov. 26, 2018, 4 pages.

Declaration of Hidefumi Kawamura dated Nov. 13, 2015 with Japanese Patent Application No. 2013-116836 filed Jun. 3, 2013.

Notice of Opposition to European Patent No. EP 3 006 049 B1 dated Nov. 26, 2018, 19 pages.

* cited by examiner

COMPOSITION FOR HOT MELT EXTRUSION AND METHOD FOR PRODUCING HOT MELT EXTRUDATE BY USING SAME

FIELD

The present invention relates to a composition for hot melt extrusion and a method for producing a hot melt extrudate by using the same.

BACKGROUND

In recent years, a method for producing a preparation comprising the step of hot melt-extruding a mixture of a drug and a polymer has been attracting attentions.

For example, a solid dispersion obtained by solidifying a poorly water-soluble drug and a polymer through hot melt extrusion, contains the drug in an amorphous state and has the drug molecularly dispersed in the polymer carrier. Such a solid dispersion has notably increased apparent solubility and improved bioavailability. Since the hot melt extrusion can be carried out in the absence of a solvent, it is applicable to a drug which is instable in water. Unnecessity for the solvent recovery in the hot melt extrusion has advantages of a safety, no environmental concerns, saving energy used for a solvent recovering step, and an improvement in a safety of the workers. Further, the hot melt extrusion enables continuous production, differing from the conventional batch production systems, and attracts attentions from the standpoint of productivity and energy consumption per hour.

One of the polymers used in the hot melt extrusion is hypromellose acetate succinate (hereinafter also referred to as "HPMCAS") obtained by introducing four kinds of the substituents in total. The HPMCAS contains two substituents of a methoxy group ($-OCH_3$) and a hydroxypropoxy group ($-OC_3H_6OH$) introduced into a cellulose skeleton to form ether structures, and two substituents of an acetyl group ($-COCH_3$) and a succinyl group ($-COC_2H_4COOH$) to form ester structures.

The contents of the respective substituents in HPMCAS listed in the Japanese Pharmacopoeia 16th Edition are defined as follows (Non-Patent Document 1).

TABLE 1

|  | Content (% by weight) | Molar substitution (MS) *1 |
|---|---|---|
| Methoxy group | 12.0 to 28.0 | 0.73 to 2.83 |
| Hydroxypropoxy group | 4.0 to 23.0 | 0.10 to 1.90 |
| Acetyl group | 2.0 to 16.0 | 0.09 to 2.30 |
| Succinyl group | 4.0 to 28.0 | 0.08 to 1.78 |

*1 The molar substitution means the average number of each of substituents introduced per glucose ring unit of cellulose.

Regarding a solid dispersion containing HPMCAS, for example, a method of lowering a glass transition temperature or a softening temperature of HPMCAS or a poorly water-soluble drug by adding water to a composition comprising HPMCAS (commercially available AS-LF having a molar substitution of 0.16 to 0.35) has been proposed, where the resulting mixture is then subjected to hot melt extrusion to form a solid dispersion (Patent Document 1).

A method for forming a preparation containing posaconazole, which is a poorly water-soluble drug, and HPMCAS (commercially available AS-MF or AS-MG having a molar substitution of 0.15 to 0.34) through hot melt extrusion (Patent Document 2), and a method for forming a preparation containing a lipid inhibitor CETP (cholesterol ester transfer protein), which is a poorly water-soluble drug, and HPMCAS (commercially available AS-MF having a molar substitution of 0.15 to 0.34) through hot melt extrusion (Patent Document 3) have been also proposed.

Further, a method for spray-drying a composition containing a poorly water-soluble drug and HPMCAS having a hydroxypropoxy molar substitution of 0.25, a succinyl molar substitution of 0.02 or more, an acetyl molar substitution of 0.65 or more, a total molar substitution of 0.85 or more with respect to acetyl and succinyl groups, and a glass transition temperature of 131 to 146° C. at relative humidity (RH) of 0% to form a solid dispersion has been proposed (Patent Document 4). Moreover, a method for spray-drying a composition containing a poorly water-soluble drug and HPMCAS having a hydroxypropoxy molar substitution of 0.21 or less, a methoxyl molar substitution of 1.45 or less, and a total molar substitution of 1.25 or more with respect to acetyl and succinyl groups to form a solid dispersion has been proposed (Patent Document 5).

PRIOR ART DOCUMENTS

Patent Document

Patent Document 1: WO 2003/077827A.
Patent Document 2: JP 2011-516612T, which is the Japanese phase publication of WO 2009/129300A.
Patent document 3: JP 2005-523895T, which is the Japanese phase publication of WO 2003/063832A.
Patent Document 4: JP 2008-501009T, which is the Japanese phase publication of WO 2005/115330A.
Patent Document 5: WO 2011/159626A.

Non-Patent Document

Non-Patent Document 1: "hypromellose acetate succinate" in Official Monographs in Supplement I to the Japanese Pharmacopoeia 16th Edition.

SUMMARY

In recent years, a solid dispersion has been required to be produced by a simpler method, and it has become necessary to lower a hot melt temperature in hot melt extrusion.

However, the method in Patent Document 1 has the disadvantages that since water is a poor solvent for a poorly water-soluble drug, the water may enhance crystallinity of the drug and prevent the drug from being amorphized, that the poorly water-soluble drug is deactivated owing to heat and humidity in a high temperature treatment, and that the drug and a carrier are liable to be hydrolyzed to become deactivated owing to influences of heat and water under a high humidity condition.

On the other hand, each method in Patent Documents 2 to 5 has the disadvantage that a free acid generated by thermal decomposition of HPMCAS owing to high temperature of the hot melt extrusion deactivates a poorly water-soluble drug, or the poorly water-soluble drug is thermally decomposed.

Particularly in the method in Patent Document 4, a mole ratio of the acetyl group to the succinyl group is high so that a solubility of HPMCAS in the small intestine is reduced, making rapid release of the drug difficult. As a result, the drug cannot stay in the small intestine in a dissolution state for a long time, reducing the bioabsorbability of the drug.

The present invention has been made in light of the above circumstances and provides a method for producing a hot melt extrudate in which the hot melt extrusion temperature lower than those of conventional hot melt extrusions prevents a drug from being deactivated owing to heat or the like and also prevents solubility of the drug from being reduced in an upper part of the small intestine, and by which a hot melt extrudate can be obtained more simply than by spray drying.

Through intense investigations for solving the above problems, the present inventors have found with respect to the four kinds of substituents in HPMCAS that selecting the hydroxypropyl molar substituent and the mole ratio of the acetyl group to the succinyl group in specific ranges makes it possible to obtain HPMCAS having a lower glass transition temperature (Tg) than those of the conventional HPMCAS, produce a hot melt extrudate at a lower hot melt extrusion temperature and prevent the extrudate from reducing its solubility in an upper part of the small intestine for allowing the drug to be rapidly released in the small intestine; and have completed the present invention.

According to the present invention, there is provided a composition for hot melt extrusion comprising a drug and hypromellose acetate succinate (HPMCAS) having a hydroxypropoxy molar substitution of 0.40 or more and a mole ratio of an acetyl group to a succinyl group of less than 1.6. Further, there is provided a method for producing a hot melt extrudate comprising the step of hot melt-extruding a composition for hot melt extrusion comprising a drug and hypromellose acetate succinate (HPMCAS) having a hydroxypropoxy molar substitution of 0.40 or more and a mole ratio of an acetyl group to a succinyl group of less than 1.6, at a hot melt temperature of not lower than a melting temperature of the hypromellose acetate succinate or of not lower than a temperature at which both the hypromellose acetate succinate and the drug are melted. The hypromellose acetate succinate can be used for producing a composition for hot melt extrusion or a hot melt extrudate.

According to the present invention, a hot melt extrudate having a high initial elution and enabling rapid release of the drug in the small intestine is obtained in which the drug stays in the small intestine in a dissolution state for a long time where the drug is efficiently absorbed, and in which the reduction in elution of the drug in an upper part of the small intestine is suppressed to enhance bioabsorbability of the drug exhibiting a high absorbability in an upper part of the small intestine. Further, since the hot melt extrusion can be carried out at a lower temperature than those in the conventional methods, a hot melt extrudate can be produced without deactivation of the drug due to heat and the like by a simpler method than spray drying or the like.

DETAILED DESCRIPTION

The present invention will be explained below in further details.

A molar substitution of the hydroxypropoxy group in HPMCAS is 0.40 or more, preferably 0.40 to 1.50, more preferably 0.40 to 1.0, further preferably 0.40 to 0.90. When a hydroxypropoxy molar substitution is less than 0.40, the hot melt extrusion temperature is elevated to bring about hydrolysis due to thermal decomposition of the hypromellose acetate succinate, and allow a part of the ester groups to be freed from the cellulose skeleton to form acetic acid and succinic acid, which deactivates the drug through their interaction with the drug.

Each content of the substituents in HPMCAS including the hydroxypropoxy group can be measured by the method described in "hypromellose acetate succinate" in Official Monographs in Supplement I to the Japanese Pharmacopoeia 16th Edition.

A glass transition temperature (Tg) of HPMCAS is preferably 115° C. or lower, more preferably 60 to 115° C., further preferably 70 to 100° C. When the glass transition temperature is higher than 115° C., the hot melt extrusion temperature is elevated as well so that the above thermal decomposition may take place.

The glass transition temperature (Tg) is measured typically by means of a differential scanning calorimeter (DSC) in the following manner. More specifically, 10 mg of HPMCAS is heated from room temperature up to 150° C. at an increase rate of 10° C./minute in a nitrogen atmosphere; further, it is once cooled down to 25° C. at a decrease rate of 10° C./minute; and then it is heated again up to 230° C. at an increase rate of 10° C./minute, thereby observing an inflection point, which is selected to be a glass transition temperature. Thus, the glass transition temperature is measured in an absolutely dry state since a moisture contained in a sample influences a measured value of Tg.

A molar substitution of the methoxy group, which is one of the substituents other than the hydroxypropoxy group in HPMCAS, is not particularly limited. The molar substitution of the methoxy group is preferably 0.70 to 2.90, more preferably 1.00 to 2.40, further preferably 1.4 to 1.9.

A molar substitution of the acetyl group in HPMCAS is not particularly limited as well. The molar substitution of the acetyl group is preferably 0.10 to 2.50, more preferably 0.10 to 1.00, further preferably 0.16 to 0.96.

A molar substitution of the succinyl group in HPMCAS is not particularly limited as well. The molar substitution of the succinyl group is preferably 0.10 to 2.50, more preferably 0.10 to 1.00, further preferably 0.10 to 0.60.

The inventors have found that when a molar substitution of the hydroxypropoxy group is elevated as described above, a dissolution pH value of HPMCAS is raised, so that solubility of HPMCAS in an upper part of the small intestine having a lower pH value than that in a lower part of the small intestine is lowered. Accordingly, the mole ratio of the acetyl group to the succinyl group is less than 1.6, preferably 0.6 to 1.5, more preferably 0.8 to 1.5, particularly preferably 0.8 to 1.3 from the standpoint of preventing the solubility of HPMCAS in an upper part of the small intestine from being reduced.

A viscosity of a dilute (0.1 mol/L) sodium hydroxide aqueous solution containing 2% by weight of HPMCAS at 20° C. is preferably 1.1 to 20 mPa·s, more preferably 1.5 to 3.6 mPa·s. When the viscosity is less than 1.1 mPa·s, the melt viscosity may be too low to receive the shearing force during the hot melt extrusion so that a piston or a screw may run idle and extrusion from a discharge port may become difficult. When the viscosity is more than 20 mPa·s, the viscosity may be too high as the viscosity of the composition for hot melt extrusion so that an excessive torque may be applied to a piston or a screw and as a result, the piston or the screw may not move or the machine may be stopped for safety. The viscosity of HPMCAS can be measured by a method described in "Viscosity Determination" in General Tests in the Japanese Pharmacopoeia 16th Edition.

HPMCAS can be produced by using a method described in, for example, JP 54-061282A. Hypromellose (another name: hydroxypropylmethyl cellulose, hereinafter also referred to as "HPMC"), which is a starting material, is dissolved in glacial acetic acid, and subjected to additions of acetic anhydride and succinic anhydride as esterifying agents and sodium acetate as a reaction catalyst for the reaction with heating. After the reaction is over, a large amount of water is added to the reaction solution to obtain a precipitate of HPMCAS. The precipitate is washed with water and then dried. When HPMC having a hydroxypropoxy molar substitution of 0.40 or more is used, the produced HPMCAS also has a hydroxypropoxy molar substitution of 0.40 or more.

The drug is not particularly limited as long as it can orally be administered. Examples of the drug include drugs for the central nervous system, drugs for the circulatory system, drugs for the respiratory system, drugs for the digestive system, antibiotics, antitussive expectorant agents, antihistamines, analgesic antipyretic anti-inflammatory drugs, diuretics, autonomic drugs, antimalarial drugs, antidiarrheal agents, psychotropic drugs, and vitamins and derivatives thereof.

Examples of the drugs for the central nervous system include diazepam, idebenone, aspirin, ibuprofen, paracetamol, naproxen, piroxicam, diclofenac, indomethacin, sulindac, lorazepam, nitrazepam, phenytoin, acetaminophen, ethenzamide, ketoprofen, and chlordiazepoxide.

Examples of the drugs for the circulatory system drugs include molsidomine, vinpocetine, propranolol, methyldopa, dipyridamole, furosemide, triamterene, nifedipine, atenolol, spironolactone, metoprolol, pindolol, captopril, isosorbide dinitrate, isosorbide mononitrate, delapril hydrochloride, meclofenoxate hydrochloride, diltiazem hydrochloride, etilefrine hydrochloride, digitoxin, propranolol hydrochloride, and alprenolol hydrochloride.

Examples of the drugs for the respiratory system include amlexanox, dextromethorphan, theophylline, pseudoephedrine, salbutamol, and guaifenesin.

Examples of the drugs for the digestive system include benzimidazole-based drugs having an anti-ulcer action, such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotics include talampicillin hydrochloride, bacampicillin hydrochloride, cefaclor, and erythromycin.

Examples of the antitussive expectorant agents include noscapine hydrochloride, carbetapentane citrate, dextromethorphan hydrobromide, isoaminile citrate, and dimemorfan phosphate.

Examples of the antihistamines include chlorpheniramine maleate, diphenhydramine hydrochloride, and promethazine hydrochloride.

Examples of the analgesic antipyretic anti-inflammatory drugs include ibuprofen, diclofenac sodium, flufenamic acid, sulpyrine, aspirin, and ketoprofen.

Examples of the diuretics include caffeine.

Examples of the autonomic drugs include dihydrocodeine phosphate, dl-methylephedrine hydrochloride, propranolol hydrochloride, atropine sulfate, acetylcholine chloride, and neostigmine.

Examples of the antimalarial drugs include quinine dihydrochloride.

Examples of the antidiarrheal agents include loperamide hydrochloride.

Examples of the psychotropic drugs include chlorpromazine.

Examples of the vitamins and the derivatives thereof include vitamin A, vitamin B1, fursultiamine, vitamin B2, vitamin B6, vitamin B12, vitamin C, vitamin D, vitamin E, vitamin K, calcium pantothenate, and tranexamic acid.

In particular, by using the HPMCAS as a carrier for a poorly water-soluble drug in a solid dispersion in accordance with the invention, the poorly water-soluble drug can improve the solubility. The term "poorly water-soluble drug" as used herein means a drug categorized as "slightly soluble", "very slightly soluble" or "practically insoluble, or insoluble" in water, which are described in the Japanese Pharmacopoeia 16th Edition. The term "slightly soluble" means that the amount of water required for dissolution with 30 minutes at 20±5° C. is 100 mL or more but less than 1000 mL when 1 g or 1 mL of a pharmaceutical in solid form is placed in a beaker, the water is poured into the beaker, and the resulting mixture is vigorously shaken for 30 seconds each time at 5-minute intervals. The term "very slightly soluble" means that the amount water required for dissolution with 30 minutes at 20±5° C. is 1000 mL or more but less than 10000 mL when measured in the same manner. The term "practically insoluble, or insoluble" means that the amount water required for dissolution with 30 minutes at 20±5° C. is 10000 mL or more when measured in the same manner.

In the above-mentioned pharmaceutical test, the dissolution of a poorly water-soluble drug means that the drug dissolves or becomes miscible in a solvent and undissolved fibers or the like are not observed or if any, only a trace amount of them is observed.

Specific examples of the poorly water-soluble drug include azole-based compounds such as itraconazole, ketoconazole, fluconazole and miconazole; dihydropyridine-based compounds such as nifedipine, nitrendipine, amlodipine, nicardipine, nilvadipine, felodipine and efonidipine; propionic acid-based compounds such as ibuprofen, ketoprofen and naproxen; and indoleacetic acid-based compounds such as indomethacin and acemetacin. Additional examples include griseofulvin, phenytoin, carbamazepine and dipyridamole.

A weight ratio of HPMCAS to the drug is not particularly limited. The weight ratio of HPMCAS to the drug is preferably from 1:0.01 to 1:100, more preferably from 1:0.1 to 1:10, still more preferably from 1:0.2 to 1:5 from the standpoint of storage stability in amorphized form.

Further, according to the invention, an additive such as a plasticizer and a surfactant may be added to the composition for improvement of moldability or the like in hot melt extrusion.

Examples of the plasticizer include acetone; methanol; ethanol; isopropanol; higher alcohols such as cetyl alcohol, and stearyl alcohol; polyhydric alcohols such as mannitol, sorbitol, and glycerin; beeswax; triethyl citrate; alkylene glycols such as polyethylene glycol, and polypropylene glycol; triacetin; dibutyl sebacate; glycerin monostearate; and monoglycerin acetate.

Examples of the surfactant include anionic surfactants such as sodium lauryl sulfate; nonionic surfactants such as diglyceride, poloxamer, polyoxyethylene sorbitan fatty acid esters (Twin 20, 60, 80), glycerin fatty acid esters, and polypropylene glycol fatty acid esters; and natural surfactants such as lecithin, and sodium taurocholate.

An amount of the plasticizer is preferably 30% by weight or less relative to the amount of HPMCAS and an amount of the surfactant is preferably 10% by weight or less relative to the amount of HPMCAS, each from the standpoint of storage stability.

The hot melt extrudate can optionally comprise a various additive which can be typically used in an ordinary manner in the field, such an excipient, a binder, a disintegrant, a lubricant, or an agglomeration preventive; and can be used in the form of an oral solid preparation such as a tablet, a granule, a fine granule and a capsule, or of an oral film agent.

Examples of the excipient include sugars such as sucrose, lactose, mannitol, and glucose; starch; and crystalline cellulose.

Examples of the binder include polyvinyl alcohol, polyacrylic acid, polyvinylpyrrolidone, hydroxyethyl cellulose, hydroxypropylmethyl cellulose, hydroxypropyl cellulose, macrogols, gum arabic, gelatin, and starch.

Examples of the disintegrant include low-substituted hydroxypropyl cellulose, carmellose or a salt thereof, croscarmellose sodium, carboxymethyl starch sodium, crospovidone, crystalline cellulose, and crystalline cellulose.carmellose sodium.

Examples of the lubricant and the agglomeration preventive include talc, magnesium stearate, calcium stearate, colloidal silica, stearic acid, waxes, hydrogenated oils, polyethylene glycols, and sodium benzoate.

The oral solid preparation obtained may be film-coated with a water-soluble coating agent such as methylcellulose and hypromellose; or enteric-coated with enteric coating agent such as hypromellose acetate succinate, hypromellose phthalate, and a methacrylate acrylate copolymer.

Next, the method for producing the hot melt extrudate will be explained.

First, a drug, HPMCAS having a hydroxypropoxy molar substitution of 0.40 or more, and an optional component are mixed to produce a composition for hot melt extrusion. The composition for hot melt extrusion produced can be extruded through a hot melt extruder to obtain an extrudate having a desirable shape such as a shape of circle or quadrangle, or a columnar or film shape.

The hot melt extruder is not particularly limited as long as it is an extruder containing a structure allowing HPMCA, the drug and the like to be heated for melting and kneaded with a sharing force of a piston or a screw in the system and allowing the resulting mixture to be extruded from a die. The hot melt extruder is preferably a biaxial type extruder from the standpoint of obtaining a more homogeneous extrudate. Specific examples of the hot melt extruder include Capirograph (uniaxial piston type extruder) produced by Toyo Seiki Seisaku-sho, Ltd.; Nano-16 (biaxial screw type extruder) produced by Leistritz AG; and Minilab (biaxial screw type extruder) and PharmaLab (biaxial screw type extruder) each produced by Thermofisher Scientific Inc.

The hot melt temperature is not particularly limited. The hot melt temperature is preferably selected in the temperature range in which the composition for hot melt extrusion can be melted and extruded smoothly, and thermal decomposition of the drug and the polymer can be avoided as much as possible. When the solid dispersion is not produced, the hot melt temperature is preferably equal to or higher than a melting temperature of HPMCAS. When the solid dispersion is produced, the hot melt temperature is preferably equal to or higher than the temperature at which both HPMCAS and the drug are melted. In addition, when a melting point of HPMCAS is lowered in the presence of the drug, the hot melt temperature is preferably equal to or higher than the temperature at which both HPMCAS and the drug are melted. More specifically, the hot melt temperature is preferably 50 to 250° C., more preferably 60 to 200° C., still more preferably 90 to 190° C. When the hot melt temperature is lower than 50° C., the composition may be melted imperfectly and difficult to be extruded. When the hot melt temperature is more than 250° C., a molecular weight of HPMCAS or the drug may be reduced owing to the thermal decomposition thereof, and the drug may be deactivated as a result of the hydrolysis of the substituents of HPMCAS.

The hot melt extrusion conditions are not particularly limited as long as the composition for hot melt extrusion having a viscosity of preferably 1 to 100000 Pa·s during the hot melt extrusion can be extruded. When a uniaxial piston type extruder is used, the extrusion speed is preferably 1 to 1000 mm/minute, more preferably 1 to 500 mm/minute. When a biaxial screw type extruder is used, the screw rotation is preferably 1 to 1000 rpm, more preferably 1 to 500 rpm. When the extrusion speed is less than 1 mm/minute, or the screw rotation is less than 1 rpm, the time of staying in the system is elongated so that thermal decomposition may take place. When the extrusion speed is more than 1000 mm/minute, or the screw rotation is more than 1000 rpm, the hot melt process in the kneading part may be insufficient so that the melting state of the drug and the polymer in the hot melt extrudate may not be uniform.

The hot melt extrudate after extruded is cooled in and after a die discharge port by naturally cooling at room temperature (1 to 30° C.) or by a cold air blown. To minimize the thermal decomposition of the drug, or to inhibit recrystallization of the amorphous drug, the extrudate is desirably cooled down rapidly to preferably 50° C. or lower, more preferably room temperature or lower (i.e. 30° C. or lower).

The hot melt extrudate after cooled may be optionally pelletized into the pellets of 0.1 to 5 mm or smaller by means of a cutter. The pellets may be further pulverized into granules or powder through the particle size control. The pulverizer may be preferably an impact mill such as a jet mill, a knife mill and a pin mill from the standpoint of being less liable to elevate the extrudate temperature due to the structure thereof. When the inside temperatures of the cutter and the pulverizer become high, HPMCAS may be thermally softened and the HPMCAS particles may adhere to each other, so that the extrudate is preferably pulverized while being cooled by a cold air blown.

EXAMPLES

The invention will be explained on basis of Examples and Comparative Examples. However, it should not be construed that the invention is limited by or to Examples.

<Synthesis of HPMCAS-1>

A 50 L kneader was charged with 12 kg of glacial acetic acid, and 6 kg of hypromellose (HPMC) having a hydroxypropoxy molar substitution of 0.97 and a methoxy molar substitution of 1.67 was added thereto and dissolved therein. Further, 3.7 kg of acetic anhydride, 2.0 kg of succinic anhydride and 4.8 kg of sodium acetate were added thereto for the reaction at 85° C. for 5 hours. Purified water 6.7 kg was added thereto and stirred, and then purified water was further added thereto to precipitate HPMCA in the form of particles. The precipitate was filtered to collect crude HPMCAS. The crude HPMCAS was washed with purified water, dried, and then sieved through a sieve of 10 mesh (opening: 1700 μm) to obtain HPMCAS-1 having final moisture content of 1.2% by weight.

The content of each substituent of HPMCAS-1 thus obtained was measured by a method described in Supplement I to the Japanese Pharmacopoeia 16th Edition. It was found to be 24.1% by weight (molar substitution of 1.00) of a hydroxypropoxy group, 16.7% by weight (molar substitution of 1.67) of a methoxy group, 5.6% by weight (molar substitution of 0.40) of an acetyl group, and 16.4% by weight (molar substitution of 0.50) of a succinyl group.

A mole ratio of an acetyl group to a succinyl group is preferably 1.6 to 4.0, more preferably 1.8 to 3.8 from the standpoint of maintaining a supersaturation state of the drug for a longer period of time.

<Synthesis of HPMCAS-2 to 7>

Using starting material HPMCs having different contents of substituents and appropriately changing the amounts of acetic anhydride and succinic anhydride, HPMCAS-2 to 7 in Table 2 were produced in the same manner.

TABLE 2

|  | molar substitution | | | | mole ratio of acetyl to succinyl |
| --- | --- | --- | --- | --- | --- |
|  | hydroxy-propoxy | methoxy | acetyl | succinyl | |
| HPMCAS-1 | 1.00 | 1.67 | 0.40 | 0.50 | 0.80 |
| HPMCAS-2 | 0.86 | 1.59 | 0.49 | 0.58 | 0.84 |
| HPMCAS-3 | 0.65 | 1.85 | 0.47 | 0.41 | 1.15 |
| HPMCAS-4 | 0.58 | 1.55 | 0.60 | 0.43 | 1.40 |
| HPMCAS-5 | 0.40 | 1.59 | 0.58 | 0.40 | 1.45 |
| HPMCAS-6 | 0.84 | 1.57 | 0.66 | 0.37 | 1.77 |
| HPMCAS-7 | 0.25 | 1.89 | 0.67 | 0.19 | 3.53 |

<Measurement of Glass Transition Temperature of HPMCAS>

The glass transition temperatures (Tg) of HPMCAS-1 to 7 were measured by means of a differential scanning calorimeter (DSC3200SA produced by Bruker Corporation). More specifically, 10 mg of each HPMCAS in a nitrogen atmosphere was heated from room temperature up to 150° C. at an increase rate of 10° C./minute, then cooled down to 25° C. at a decrease rate of 10° C./minute, and heated again up to 230° C. at an increase rate of 10° C./minute. Consequently, an endothermic and exothermic curve was obtained, and a temperature of an inflection point in the curve, which was the temperature of an inflection point measured in the second temperature increase, was selected to be a glass transition temperature.

Examples 1 to 5 and Comparative Examples 1 to 2

HPMCAS-1 to 7 were dried in advance so that moisture contents were measured to be less than 1% by weight. The dried HPMCAS-1 to 7 were extruded from a die of a discharge port in a vacuum extruder (uniaxial piston type melt extruder: Capirograph produced by Toyo Seiki Seisaku-sho, Ltd.) using a die diameter of 1 mm, a die height of 10 mm and an extrusion rate of 50 mm/minute, and the lowest extrusion temperatures of HPMCAS-1 to 7 were measured. The results thereof are shown in Table 3.

TABLE 3

|  | HPMCAS | glass transition temp. (° C.) | lowest extrusion temp. (° C.) |
| --- | --- | --- | --- |
| Example 1 | HPMCAS-1 | 70 | 110 |
| Example 2 | HPMCAS-2 | 81 | 140 |
| Example 3 | HPMCAS-3 | 94 | 140 |
| Example 4 | HPMCAS-4 | 101 | 140 |
| Example 5 | HPMCAS-5 | 112 | 150 |
| Comp. Ex. 1 | HPMCAS-6 | 85 | 140 |
| Comp. Ex. 2 | HPMCAS-7 | 126 | 180 |

HPMCAS having a hydroxypropoxy molar substitution of 0.40 or more, which were used in Examples 1 to 5 and Comparative Example 1, were low in the glass transition temperature and also low in the lowest extrusion temperature in comparison with HPMCAS having a hydroxypropoxy molar substitution of less than 0.40, which was used in Comparative Example 2.

It is evident from the above results that according to the invention, the composition for hot melt extrusion can be extruded at lower temperatures so that the extrudate can be obtained without thermal decomposition of the drug.

Examples 6 to 10 and Comparative Examples 3 to 4

Using ascorbic acid, which is a water-soluble drug, hot melt extrudates were produced. The ascorbic acid has a thermal decomposition temperature of 176° C., and is a model drug which creates concern about deactivation owing to thermal decomposition during hot melt extrusion.

Each HPMCAS and ascorbic acid powder were mixed at a weight ratio of HPMCAS to ascorbic acid of 1:0.5 in a mortar to produce a composition for hot melt extrusion.

Next, the above mixed powder was subjected to the hot melt extrusion at 130° C. or higher by means of a hot melt extruder (HAAKE MiniLab produced by Thermofisher Scientific Inc.) having a co-rotation biaxial screw (diameter of 5/14 mm, length of 109.5 mm, screw revolution of 100 rpm, residence time of 5 minutes). The lowest extrusion temperature of the hot melt extrudate was measured in the same manner as in Example 1. Further, the hot melt extrudate thus obtained was pulverized at 20000 rpm by means of a pulverizer (Wonder Blender WB-1 produced by Osaka Chemical Co., Ltd.) and sieved through a sieve of 30 mesh (opening of 500 μm). The powder thus obtained and the composition for hot melt extrusion before the extrusion were subjected to measurement of a yellowness index (YI) by means of an SM color computer (SM-T produced by Suga Test Instruments Co., Ltd.). The results thereof are shown in Table 4.

TABLE 4

|  | HPMCAS | yellowness index (YI) | | lowest extrusion temp. (° C.) |
| --- | --- | --- | --- | --- |
|  |  | before extrusion | after extrusion | |
| Example 6 | HPMCAS-1 | 16.9 | 17.2 | 130 |
| Example 7 | HPMCAS-2 | 16.8 | 18.5 | 145 |
| Example 8 | HPMCAS-3 | 16.8 | 18.8 | 150 |
| Example 9 | HPMCAS-4 | 16.8 | 19.0 | 150 |
| Example 10 | HPMCAS-5 | 16.8 | 19.1 | 150 |
| Comp. Ex. 3 | HPMCAS-6 | 16.8 | 18.7 | 145 |
| Comp. Ex. 4 | HPMCAS-7 | 16.8 | 29.9 | 160 |

In Examples 6 to 10 and Comparative Example 3, in which the compositions containing HPMCAS having a hydroxypropoxy molar substitution of 0.40 or more were used, the lowest extrusion temperature was able to be reduced by 26° C. or more than the thermal decomposition temperature (176° C.) of ascorbic acid; the appearances of the hot melt extrudates obtained were not changed from the white color and had a yellowness index (YI) of 20 or less, which was almost the same as that (YI=16.8) of the mixed powder before the extrusion; and the ascorbic acid was not thermally decomposed through the hot melt extrusion and not deactivated. On the other hand, in Comparative Example 4, in which the composition containing HPMCAS was used, the lowest extrusion temperature was 160° C., which was higher than those in Examples 6 to 10 and Comparative Example 3; the appearance of the hot melt extrudate obtained was changed from the white color of the starting material powder to a brown color and had a yellowness index (YI) which exceeded 20 to a large extent; and it was confirmed that the ascorbic acid was thermally decomposed through the hot melt extrusion and deactivated.

Examples 11 to 15 and Comparative Examples 5 to 6

Film test pieces were prepared by using HPMCAS-1 to 7 and subjected to measurement of a dissolution time in a phosphate buffer solution. A solution of 16 g HPMCAS in 64 g of a mixed solvent of methylene chloride and ethanol at the weight ratio of methylene chloride to ethanol of 1:1 was cast on a glass plate and dried at room temperature. The resulting film was dried at 80° C. for 2 hours, and was cut into a test piece having a thickness of 100 μm, a length of 1 cm and a width of 1 cm.

A dissolution time of the test piece was measured in accordance with Disintegration Test (auxiliary tube) in the Japanese Pharmacopoeia 16th Edition. More specifically, one of the test pieces was placed in 1 L of a phosphate buffer solution having a pH value of 6.0, and subjected to measurement of the time required for the test piece to be dissolved to observe no undissolved matter by means of a Japanese Pharmacopoeia disintegration tester (NT-400 produced by Toyama Sangyo Co., Ltd.). The phosphate buffer solution had the pH value of 6.0 corresponding to that of a digestive juice in an upper part to a middle part of the small intestine as described in U.S. Pharmacopoeia 36. The results thereof are shown in Table 5.

TABLE 5

|  | HPMCAS | film dissolution time (minutes) |
|---|---|---|
| Example 11 | HPMCAS-1 | 63.2 |
| Example 12 | HPMCAS-2 | 44.4 |
| Example 13 | HPMCAS-3 | 38.9 |
| Example 14 | HPMCAS-4 | 36.7 |
| Example 15 | HPMCAS-5 | 25.3 |
| Comp. Ex. 5 | HPMCAS-6 | 120 or more |
| Comp. Ex. 6 | HPMCAS-7 | 120 or more |

The drug is preferably rapidly dissolved in an upper part of the small intestine for more efficient absorption of the drug, and is particularly preferably dissolved in shorter than 120 minutes. In Comparative Example 5, the test piece containing HPMCAS having the mole ratio of acetyl to succinyl of 1.77 and a molar hydroxypropoxy substitution of 0.84 required a long time for dissolution, and the undissolved test piece was present even after 120 minutes. This is considered to be attributable to that a dissolution pH of HPMCAS is raised owing to the high mole ratio of acetyl to succinyl and the increased hydroxypropoxy molar substitution, so that the solubility of the drug in a phosphate buffer solution having the pH value of 6.0 corresponding to that of a digestive juice in an upper part to a middle part of the small intestine having a relatively low pH was lowered. In Comparative Example 6, the test piece containing HPMCAS having the mole ratio of acetyl to succinyl of more than 3.5 exhibited the decrease of the solubility in the phosphate buffer solution, and the undissolved test piece was present even after 120 minutes. It is because the molar substitution of the hydrophilic succinyl group is small and the molar substitution of the hydrophobic acetyl group is large.

On the other hand, in Examples 11 to 15, the test pieces having the mole ratio of acetyl to succinyl of less than 1.6 were more rapidly dissolved in the phosphate buffer solution of pH 6.0 though the hydroxypropoxy molar substitution was 0.4 or more, in comparison with the test pieces prepared in the comparative examples, and it took shorter than 53 minutes until the test pieces were dissolved.

It is evident from the above results that the test pieces can be rapidly dissolved in an upper part of the small intestine by selecting the mole ratio of acetyl to succinyl to be in the specific range. In addition, HPMCAS having a hydroxypropoxy molar substitution of 0.40 or more has the increased dissolution pH, but can be rapidly dissolved in an upper part of the small intestine.

Examples 16 to 20 and Comparative Examples 7 to 8

Each HPMCAS and ketoconazole having melting point of 148° C., which is a poorly water-soluble drug, were mixed at the weight ratio of the HPMCAS to the ketoconazole of 1:1 in a mortar to produce a composition for hot melt extrusion.

Next, the above mixed powder was subjected to hot melt extrusion at 150° C. by means of the hot melt extruder (HAAKE MiniLab produced by Thermofisher Scientific Inc.) having a co-rotation biaxial screw (diameter of 5/14 mm, length of 109.5 mm, screw rotation of 100 rpm, residence time of 5 minutes). The hot melt extrude thus obtained was pulverized at 20000 rpm by means of the pulverizer (Wonder Blender WB-1 produced by Osaka Chemical Co., Ltd.) and sieved through a sieve of 30 mesh (opening of 500 μm). The powder thus obtained was subjected to Elution Test in the Japanese Pharmacopoeia 16th Edition.

An elution ratio (% by weight) of ketoconazole eluted from 180 mg of the powder, which corresponds to 90 mg of ketoconazole, was measured at a paddle rotation of 100 rpm by using 900 mL of a phosphate buffer solution having a pH value of 6.0 described in U.S. Pharmacopoeia 36 and a Japanese Pharmacopoeia elution tester (NTR-6100A produced by Toyama Sangyo Co., Ltd.). The elution ratio of ketoconazole was quantitatively determined from a UV absorbance at the wavelength of 225 nm and the optical pass length of 10 mm on basis of an absorbance-conversion straight line prepared in advance by measuring UV absorbance values of the known concentrations of ketoconazole. The results thereof are shown in Table 6.

TABLE 6

|  |  | elution ratio (% by weight) of ketoconazole *1 | | | | |
|---|---|---|---|---|---|---|
|  | HPMCAS | 0 minutes | 10 minutes | 30 minutes | 60 minutes | 90 minutes |
| Example 16 | HPMCAS-1 | 0 | 15.3 | 32.4 | 44.6 | 51.6 |
| Example 17 | HPMCAS-2 | 0 | 29.0 | 54.9 | 68.1 | 75.7 |
| Example 18 | HPMCAS-3 | 0 | 12.2 | 30.0 | 41.7 | 51.3 |
| Example 19 | HPMCAS-4 | 0 | 18.3 | 39.6 | 54.3 | 62.4 |
| Example 20 | HPMCAS-5 | 0 | 30.0 | 51.3 | 66.0 | 72.1 |
| Comp. Ex. 7 | HPMCAS-6 | 0 | 6.6 | 13.7 | 21.3 | 26.4 |
| Comp. Ex. 8 | HPMCAS-7 | 0 | 6.1 | 12.2 | 17.8 | 21.8 |

*1 It shows the elution ratio of ketoconazole at the respective elution test times (minutes).

In Examples 16 to 20, the compositions containing HPMCAS having a mole ratio of acetyl to succinyl of less than 1.6 exhibited the high elution ratio of 50% by weight or more even after 90 minutes.

On the other hand, in Comparative Examples 7 and 8, the composition containing HPMCAS having a hydroxypropoxy molar substitution of 0.40 or more and a mole ratio of acetyl to succinyl of 1.6 or more, and the composition containing HPMCAS having a mole ratio of acetyl to succinyl of more than 3.5 stayed in the low elution ratio of 27% by weight or less even 90 minutes after the test started.

It is considered from the above results that by selecting a mole ratio of acetyl to succinyl to be less than 1.6, the solubility of HPMCAS in an aqueous solution having a relatively low pH value such as that of an upper part of the small intestine is improved so that the elution is increased.

Further, the hot melt extrudate obtained was pulverized at 20000 rpm by means of a small-sized desktop pulverizer (Wonder Blender WB-1 produced by Osaka Chemical Co., Ltd.) and sieved through a sieve of 30 mesh (opening of 500 μm). The powder thus obtained was subjected to measurement of an X ray diffraction image to find that a crystal peak of ketoconazole was not observed in the X ray diffraction images and the elution ratio of ketoconazole was notably high. It is evident from the above facts that the composition obtained by hot melt extrusion forms a solid dispersion having the ketoconazole dispersed in HPMCAS, the ketoconazole being in an amorphous state.

The invention claimed is:

1. A composition for hot melt extrusion comprising a drug and hypromellose acetate succinate having a hydroxypropoxy molar substitution of 0.40 or more and a mole ratio of an acetyl group to a succinyl group of less than 1.6.

2. The composition for hot melt extrusion according to claim 1, wherein the hypromellose acetate succinate has a glass transition temperature Tg of 115° C. or lower.

3. The composition for hot melt extrusion according to claim 1, wherein the drug is a poorly water-soluble drug.

4. A method for producing a hot melt extrudate comprising the step of hot melt-extruding a composition for hot melt extrusion comprising a drug and hypromellose acetate succinate having a hydroxypropoxy molar substitution of 0.40 or more and a mole ratio of an acetyl group to a succinyl group of less than 1.6, at a hot melt temperature of not lower than a melting temperature of the hypromellose acetate succinate or of not lower than a temperature at which both the hypromellose acetate succinate and the drug are melted.

5. The method for producing a hot melt extrudate according to claim 4, wherein the hot melt temperature is 50 to 250° C.

6. The composition for hot melt extrusion according to claim 1, Therein the hydroxypropoxy molar substitution is 0.40 to 0.90.

7. The composition for hot melt extrusion according to claim 1, wherein the mole ratio of an acetyl group to a succinyl group is 0.8 to 1.3.

8. The composition for hot melt extrusion according to claim 3, wherein the poorly water-soluble drug is one or more of itraconazole, ketoconazole, fluconazole, miconazole, nifedipine, nitrendipine, amlodipine, nicardipine, nilvadipine, felodipine, efonidipine, ibuprofen, ketoprofen, naproxen, indomethacin, acemetacin, griseofulvin, phenytoin, carbamazepine and dipyridamole.

9. The composition for hot melt extrusion according to claim 1, further comprising a plasticizer.

10. The composition for hot melt extrusion according to claim 1, further comprising a surfactant.

* * * * *